United States Patent [19]

Buck

[11] Patent Number: 5,583,092
[45] Date of Patent: Dec. 10, 1996

[54] HERBICIDAL [1,2,4] THIADIAZOLES

[75] Inventor: Wolfgang Buck, Ingelheim, Germany

[73] Assignee: American Cyanamid Company, Madison, N.J.

[21] Appl. No.: 441,565

[22] Filed: May 15, 1995

[30] Foreign Application Priority Data

Feb. 8, 1995 [EP] European Pat. Off. ............ 95101693

[51] Int. Cl.$^6$ ............ C07D 285/08; A01N 43/836
[52] U.S. Cl. ............ 504/262; 504/253; 546/268.7; 546/256; 548/128
[58] Field of Search ............ 548/128; 546/277; 504/253, 262

[56] References Cited

U.S. PATENT DOCUMENTS

| | | | |
|---|---|---|---|
| 3,573,317 | 3/1971 | Schmidt | 548/128 |
| 3,770,749 | 11/1973 | Phillips | 548/128 |
| 3,859,296 | 1/1975 | Phillips | 548/128 |

FOREIGN PATENT DOCUMENTS

| | | | |
|---|---|---|---|
| 0748370 | 2/1995 | Japan | 546/194 |
| WO94/20477 | 9/1994 | WIPO . | |

OTHER PUBLICATIONS

R. Paton, et al, J. Chem. Soc., Chem. Commun., 714, (1980).
R. Paton, et al., Phosph. and Sulphur, 15, 137 (1983).
P. A. Brownsort, et al., J. Chem. Soc., Perkin Trans., 2339 (1987).
R. K. Howe, et al., J. Org. Chem., 39, 962, (1974).
J. E. Franz, et al., J. Org. Chem., 41, 620 (1976).
R. K. Howe, et al., J. Org. Chem., 42, 1813 (1977).
Karady, Heterocycles, 24 (5) 1193(1986).

Primary Examiner—Robert Gerstl
Attorney, Agent, or Firm—John W. Hogan, Jr.

[57] ABSTRACT

Novel herbicidal compounds of the general formula

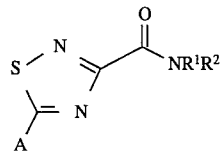
(I)

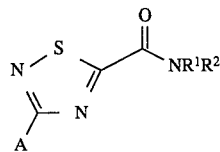

(II)

wherein A represents an optionally substituted alkyl, alkenyl, cycloalkyl, cycloalkenyl, aryl, heteroaryl, aralkyl or heteroaralkyl group; $R^1$ represents a hydrogen atom or an acyl group; and $R^2$ represents an optionally substituted alkyl, alkenyl, aryl, heteroaryl, aralkyl or heteroaralkyl group.

6 Claims, No Drawings

HERBICIDAL [1,2,4] THIADIAZOLES

This invention relates to certain novel amides of [1,2,4] thiadiazole-carboxylic acids, to the preparation of such compounds, to herbicidal compositions containing such compounds, and to a method of combating undesired plant growth using such compounds.

Two U.S. Pat. Nos. 3,770,749 and 3,859,296, describe certain amides of 3-substituted [1,2,4]thiadiazole-5-carboxylic acids and the herbicidal activities thereof. In both of these patents, the amides are defined as being tertiary amides, i.e. bearing two N-alkyl and/or N-aryl groups. The compounds are alleged to have herbicidal activity against various species when applied at a dosage from 2 to 25 pounds per acre; however, no actual example for this activity has been reported. Thus, from neither of these patents might one reasonably infer that secondary amides or imides derived from 3-substituted [1,2,4]thiadiazole-5-carboxylic acids could be particularly advantageous in terms of control of undesired plants and tolerance by crops.

We have now found that, surprisingly, secondary [1,2,4] thiadiazole-5-carboxamides and respective imides as well as [1,2,4]thiadiazole-3-carboxamides and respective imides show excellent herbicidal activity at and below dosages which are significantly lower than the ranges claimed in the aforementioned patents (for example at 800 g/ha which corresponds to about 0.71 lb/acre), combined with a good selectivity in crops.

Accordingly, the present invention provides novel compounds of the general formula

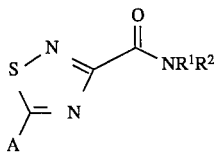

(I)

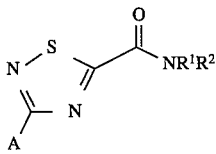

(II)

wherein A represents an optionally substituted alkyl, alkenyl, cycloalkyl, cycloalkenyl, aryl, heteroaryl, aralkyl or heteroaralkyl group; $R^1$ represents a hydrogen atom or an acyl group; and $R^2$ represents an optionally substituted alkyl, alkenyl, aryl, heteroaryl, aralkyl or heteroaralkyl group.

Generally, when any of the above mentioned moieties comprises an alkyl group this alkyl group may be linear or branched and may suitably contain 1 to 10, preferably 1 to 6 carbon atoms. Examples of such groups are methyl, ethyl, n-propyl, i-propyl, n-butyl, i-butyl, s-butyl, t-butyl, n-pentyl, i-pentyl, s-pentyl and neopentyl groups. An alkenyl group may suitably contain 2 to 8 carbon atoms. A cycloalkyl or cycloalkenyl group may have from 3 to 8 carbon atoms, most preferably 3 to 6 carbon atoms, and especially 5 or 6. An acyl group consists of a carbonyl group connected to an optionally substituted alkyl, aryl or heteroaryl group and suitably contains 2 to 8 carbon atoms.

An aralkyl group consists of an alkyl group, defined as above, substituted by an aryl group. An aryl group may suitably contain from 6 to 10 carbon atoms and is preferably a phenyl or a naphthyl group. A heteroaralkyl group consists of an alkyl group, defined as above, substituted by a heteroaryl group. A heteroaryl group may be mono- or polycylic. It suitably comprises 5- and/or 6-membered heterocycles, containing one or more sulphur and/or nitrogen and/or oxygen atoms. Any or all of the constituent groups may be optionally substituted.

When any groups are designated as being optionally substituted, the substituent groups which are optionally present may be any of those customarily employed in the development of pesticidal compounds, and/or the modification of such compounds to influence their structure/activity, persistence, penetration or other property. In relation to moieties defined above as comprising an optionally substituted alkyl, alkenyl or cycloalkyl group, including alkyl parts of aralkyl, heteroaralkyl or acyl groups, specific examples of such substituents include halogen, especially fluorine, chlorine or bromine atoms, and nitro, cyano, hydroxyl, $C_{1-4}$ alkoxy, $C_{1-4}$ haloalkoxy, ($C_{1-4}$ alkoxy)carbonyl groups, phenyl, amino, alkyl- and phenyl-sulphinyl, phenyl-sulphenyl and phenyl-sulphonyl groups, and mono- or di-($C_{1-4}$ alkyl)amino groups. It is preferred, however, that such moieties are unsubstituted, or halogen-substituted.

In relation to moieties defined above as comprising an optionally substituted aryl or heteroaryl group, including aryl and heteroaryl parts of aralkyl, heteroaralkyl and acyl groups, optional substituents include halogen, especially fluorine, chlorine and bromine atoms, and nitro, cyano, amino, hydroxyl, $C_{1-4}$ alkyl, $C_{1-4}$ haloalkyl (especially $CF_3$), $C_{1-4}$ alkoxy and $C_{1-4}$ haloalkoxy groups. 1 to 5 substituents may suitably be employed.

The compounds are oils, gums, or, predominantly, crystalline solid materials. They are superior through their valuable herbicidal properties. For example, they can be used in agriculture or related fields for the control of undesired plants. The compounds of general formula I and II according to the invention possess a high herbicidal activity within a wide concentration range and at relatively low dosages.

Suitably, A represents an optionally substituted alkyl, cycloalkyl, alkenyl, dialkylamino, phenyl, pyridyl, furyl or thienyl group.

Preferably, A represents an optionally substituted $C_{2-6}$ alkyl group or $C_{2-6}$ alkenyl group, a phenyl group which is unsubstituted, or substituted by one or more moieties independently selected from halogen atoms, $C_{1-4}$ alkyl groups, $C_{1-4}$ alkoxy groups and $C_{1-4}$ haloalkyl groups, or a pyridine group which is unsubstituted, or substituted by a halogen atom.

Most preferably, A represents a tert-butyl group, an isobutyl group, an isopropyl group, a 2-methoxyethyl group, a styryl group, a phenyl group which is unsubstituted, or substituted by one or two moieties selected from fluorine and chlorine atoms, trifluoromethyl groups and methoxy groups, or a pyridyl group which is optionally substituted by a chlorine atom.

Preferably, $R^1$ represents a hydrogen atom.

Suitably, $R^2$ represents an optionally substituted alkyl, or alkenyl group, or an optionally substituted aryl, aralkyl or heteroaralkyl group.

Preferably, $R^2$ represents an optionally substituted $C_{2-6}$ alkyl group; a $C_{2-6}$ alkenyl group; a phenyl group, which is optionally substituted by 1–2 halogen atoms; a 1,2,3,4-tetrahydronaphthalene group; a phenylalkylene group, in which the phenyl moiety is optionally substituted by 1 or 2 moieties independently selected from halogen and $C_{1-4}$ alkyl, and the alkylene moiety is a methylene group or a $C_{2-4}$ alkylene group, which is straight chained or branched; or a heteroarylalkylene group, in which the heteroaryl moiety is a furyl, pyridyl, thienyl or benzothiophene group, optionally substituted by 1 or 2 moieties selected from halogen and $C_{1-4}$ alkyl, the alkylene moiety being as defined for a phenyl-alkylene group.

In general, preferred groups $R^2$ conform to the general formula

wherein $R^3$ represents a hydrogen atom or an optionally substituted $C_{1-2}$ alkyl group, and $R^4$ represents an optionally substituted phenyl group, or an optionally substituted pyridyl, furyl, thienyl or benzothiophene group.

Preferably, $R^3$ represents a hydrogen atom or a methyl group and $R^4$ represents an unsubstituted phenyl group or a thienyl group which is optionally substituted by a methyl group.

Included in the scope of the present invention are (R) and (S) isomer of compounds of general formula I and II having an optical centre, and salts, N-oxides and acid addition compounds.

Particularly interesting activity has been found in (S)-isomer compounds of general formula I or II wherein $R^2$ represents the group —$CH(R^3)R^4$, of which the C atom is the stereogenic center.

The invention is exemplified by the following specific compounds:

(R/S)-3-Isopropyl-[1,2,4]thiadiazole-5-carboxylic acid, [1-(2-thienyl)ethyl]amide;
(S)-3-(4-Methoxyphenyl)-[1,2,4]thiadiazole-5-carboxylic acid, 1-(phenylethyl)amide;
(R/S)-5-(3-Trifluoromethyl-phenyl)-[1,2,4]thiadiazole-3-carboxylic acid, [1-(2-thienyl)ethyl]amide;
(R/S)-3-Phenyl-[1,2,4]thiadiazole-5-carboxylic acid, [1-(2-thienyl)ethyl]amide;
(S)-3-(4-Methoxyphenyl)-[1,2,4]thiadiazole-5-carboxylic acid, 1-(phenylethyl)amide;
(R/S) -3-tert-Butyl-[1,2,4]thiadiazole-5-carboxylic acid, [1-(2-thienyl)ethyl]amide;
(S)-3-tert-Butyl-[1,2,4]thiadiazole-5-carboxylic acid, 1-(phenylethyl)amide;
(S)-3-Isopropyl-[1,2,4]thiadiazole-5-carboxylic acid, 1-(phenylethyl)amide;
(R/S)-3-Isobutyl-[1,2,4]thiadiazole-5-carboxylic acid, [1-(2-thienyl)ethyl]amide;
(S)-3-Isobutyl-[1,2,4]thiadiazole-5-carboxylic acid, 1-(phenylethyl)amide;
(R/S)-3-(4-Fluorophenyl)-[1,2,4]thiadiazole-5-carboxylic acid, [1-(2-thienyl)ethyl]amide;
(S)-3-(4-Fluorophenyl)-[1,2,4]thiadiazole-5-carboxylic acid, 1-(phenylethyl)amide;
(R/S)-3-(3-Trifluoromethylphenyl)-[1,2,4]thiadiazole-5-carboxylic acid, [1-(2-thienyl)ethyl]amide;
(R/S)-5-(4-Chlorophenyl)-[1,2,4]thiadiazole-3-carboxylic acid, [1-(2-thienyl)ethyl]amide;
(S)-3-(4-Chlorophenyl)-[1,2,4]thiadiazole-5-carboxylic acid, 1-(phenylethyl)amide;
(S)-3-(2-Fluorophenyl)-[1,2,4]thiadiazole-5-carboxylic acid, 1-(phenylethyl)amide;
(S)-5-(4-Fluorophenyl)-[1,2,4]thiadiazole-3-carboxylic acid, 1-(phenylethyl) amide;
(S)-3-(3-Fluorophenyl)-[1,2,4]thiadiazole-5-carboxylic acid, 1-(phenylethyl)amide;
(S)-3-(6-Chloro-2-pyridyl)-[1,2,4]thiadiazole-5-carboxylic acid, 1-(phenylethyl)amide;
(S)-5-(Phenyl)-[1,2,4]thiadiazole-3-carboxylic acid, 1-(phenylethyl)amide;
(R/S)-5-(4-Methoxyphenyl)-[1,2,4]thiadiazole-3-carboxylic acid, [1-(2-thienyl)ethyl]amide;
(R/S)-3-Isopropyl-[1,2,4]thiadiazole-5-carboxylic acid, [1-(2-thienyl)ethyl]amide;
(S)-5-(2-Fluorophenyl)-[1,2,4]thiadiazole-3-carboxylic acid, 1-(phenylethyl)amide;
(R/S)-5-(2-Fluorophenyl)-[1,2,4]thiadiazole-3-carboxylic acid, [1-(2-thienyl)ethyl]amide;
(R/S)-3-(2,6-Difluorophenyl)-[1,2,4]thiadiazole-5-carboxylic acid, [1-(2-thienyl)ethyl]amide; and
(S)-3-(2,6-Difluorophenyl)-[1,2,4]thiadiazole-5-carboxylic acid, 1-(phenylethyl)amide.

The invention also provides a process for the preparation of a compound of general formula I or II, which comprises reacting a respective compound of the general formula III or IV

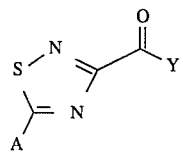 (III)

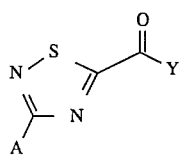 (IV)

wherein A is as defined above and Y represents a leaving group, with a compound of general formula V

 (V)

wherein $R^1$ and $R^2$ are as defined above.

A suitable leaving group Y is a halogen atom, especially chlorine; an acyloxy group, for example, acetoxy; an alkoxy group, suitably a methoxy or ethoxy group; or an aryloxy group, for example, a phenoxy group. Preferably, Y is a methoxy or ethoxy group.

In practice, the reaction may be carried out in the absence or presence of a solvent which promotes the reaction or at least does not interfere with it, for example toluene, xylene, ethanol, methanol, isopropanol. Mixtures thereof may also be employed.

When Y is an alkoxy group, the reaction is suitably carried out in an organic solvent, for example ethanol or toluene, and within a temperature range from room temperature to the boiling point of the mixture. The reaction has been found to work most effectively when carried out under basic conditions. The basic conditions can suitably be provided by employing an excess of the amine V in the reaction, suitably a twofold excess of V with respect to III or IV. Alternatively, the basic conditions can be provided by the separate inclusion of a base in the reaction mixture with V and III or IV. The base may be any of those commonly employed in organic chemistry, for instance, a hydroxide, hydride, alkoxide, carbonate or hydrogen carbonate salt of a metal from Groups I or II of the Periodic Table; or an amine. A particularly suitable base is a tertiary amine, for example triethylamine.

In a variation of the above process, a compound of formula I or II is prepared by reacting a respective compound of formula III or IV with a salt of general formula VI

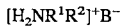 (VI wherein $R^1$ and $R^2$ are as defined previously and $B^-$ is a general anionic species, in the presence of a base. The reaction is suitably carried out in an organic solvent, for example ethanol or toluene, and within a temperature range from room temperature to the boiling point of the mixture. The base may be any of those commonly employed in organic chemistry, for instance, a hydroxide, hydride, alkoxide, carbonate or hydrogen carbonate salt of a metal from Groups I or II of the Periodic Table; or an amine. A particularly suitable base is a tertiary amine, for example triethylamine, which may be present in a several-fold excess, for example four-fold.

Many starting [1,2,4]thiadiazole-5-carboxylates IV (Y=alkoxy) are known or may be prepared for example by known methods, such as those described by R. M. Paton et al, *J. Chem. Soc., Chem. Commun.*, 714, (1980) and *J. Chem. Soc., Perkin Trans.*, 1517, (1985); R. M. Paton et al, *Phosph. and Sulphur*, 15, 137, (1983); P. Brownsort et al, *J. Chem. Soc., Perkin Trans.*, 2339, (1987); R. K. Howe et al, *J. Org. Chem.*, 39, 962, (1974); and J. E. Franz et al, *J. Org. Chem.*, 41, 620, (1976).

Some starting [1,2,4]thiadiazole-3-carboxylates III (A=aryl, Y=alkoxy) are known or they may be prepared for example analogously to the method of R. K. Howe et al, *J. Org. Chem.*, 42, 1813, (1977).

The amines of formula V and the salts of formula VI are known or may be obtained from known materials by standard techniques.

The compounds of general formula I and II have been found to show interesting activity as herbicides. Accordingly, the invention further provides a herbicidal composition comprising a compound of formula I as defined above in association with at least one carrier, and a method of making such a composition which comprises bringing a compound of formula I into association with at least one carrier. Preferably there are at least two carriers, at least one of which is a surface-active agent.

The invention also provides a method of combating undesired plant growth at a locus, comprising application of such a compound or composition.

Particularly interesting activity has been found against grasses and broad leaf weeds, pre- and postemergence. Selectivity in important crop species such as wheat, barley, maize, rice and soybeans has also been found. This activity provides a further aspect of the present invention.

In a method as mentioned above, the dosage of the active ingredient, the compound of general formula I, may, for example, be from 0.01 to 10 kg/ha, suitably 0.05 to 4 kg/ha, preferably 0.05 to 1 kg/ha. The locus may be an agricultural or horticultural locus, comprising, for example, a plant or soil. In a preferred method the locus contains undesired plant growth and treatment is by foliar spray application.

The invention also provides the use of a compound as defined above, as a herbicide. A carrier in a composition according to the invention is any material with which the active ingredient is formulated to facilitate application to the locus to be treated, or to facilitate storage, transport or handling. A carrier may be a solid or a liquid, including a material which is normally gaseous but which has been compressed to form a liquid, and any of the carriers normally used in formulating pesticidal compositions may be used. Preferably compositions according to the invention contain 0.5 to 95% by weight of active ingredient.

Suitable solid carriers include natural and synthetic clays and silicates, for example natural silicas such as diatomaceous earths; magnesium silicates, for example talcs; magnesium aluminium silicates, for example attapulgites and vermiculites; aluminium silicates, for example kaolinites, montmorillonites and micas; calcium carbonate; calcium sulphate; ammonium sulphate; synthetic hydrated silicon oxides and synthetic calcium or aluminium silicates; elements, for example carbon and sulphur, natural and synthetic resins, for example coumarone resins, polyvinyl chloride, and styrene polymers and copolymers; solid polychlorophenols; bitumen; waxes; and solid fertilisers, for example superphosphates.

Suitable liquid carriers include water, alcohols, for example isopropanol and glycols; ketones, for example acetone, methyl ethyl ketone, methyl isobutyl ketone and cyclohexanone; ethers; aromatic or araliphatic hydrocarbons, for example benzene, toluene and xylene; petroleum fractions, for example kerosene and light mineral oils; chlorinated hydrocarbons, for example carbon tetrachloride, perchloroethylene and trichloroethane. Mixtures of different liquids are often suitable.

Agricultural compositions are often formulated and transported in a concentrated form which is subsequently diluted by the user before application. The presence of small amounts of a carrier which is a surface-active agent facilitates this process of dilution. Thus, preferably at least one carrier in a composition according to the invention is a surface-active agent. For example the composition may contain at least two carriers, at least one of which is a surface-active agent.

A surface-active agent may be an emulsifying agent, a dispersing agent or a wetting agent; it may be non-ionic or ionic. Examples of suitable surface-active agents include the sodium or calcium salts of polyacrylic acids and lignin sulphonic acids; the condensation products of fatty acids or aliphatic amines or amides containing at least 12 carbon atoms in the molecule with ethylene oxide and/or propylene oxide; fatty add esters of glycerol, sorbitan, sucrose or pentaerythritol; condensates of these with ethylene oxide and/or propylene oxide; condensation products of fatty alcohol or alkyl phenols, for example p-octylphenol or p-octylcresol, with ethylene oxide and/or propylene oxide; sulphates or sulphonates of these condensation products; alkali or alkaline earth metal salts, preferably sodium salts, of sulphuric or sulphonic acid esters containing at least 10 carbon atoms in the molecule, for example sodium lauryl sulphate, sodium secondary alkyl sulphates, sodium salts of sulphonated castor oil, and sodium alkaryl sulphonates such as dodecylbenzene sulphonate; and polymers of ethylene oxide and copolymers of ethylene oxide and propylene oxide.

The compositions of the new invention may for example be formulated as wettable powders, dusts, granules, solutions, emulsifiable concentrates, emulsions, suspension concentrates and aerosols. Wettable powders usually contain 25, 50 or 75% w/w of active ingredient and usually contain in addition to solid inert carrier, 3–10% w/w of a dispersing agent and, where necessary, 0–10% w/w of stabiliser(s) and/or other additives such as penetrants or stickers. Dusts are usually formulated as a dust concentrate having a similar composition to that of a wettable powder but without a dispersant, and are diluted in the field with further solid carrier to give a composition usually containing 0.5–10% w/w of active ingredient. Granules are usually prepared to have a particle size between 10 and 100 BS mesh (1.676–0.152 mm), and may be manufactured by agglomeration or impregnation techniques. Generally, granules will contain 0.5–75% w/w active ingredient and 0–10% w/w of additives such as stabilisers, surfactants, slow release modifiers and binding agents. The so-called 'dry flowable powders' consist of relatively small granules having a relatively higher concentration of active ingredient. Emulsifiable concentrates usually contain, in addition to a solvent and, when necessary, co-solvent, 10–50% w/v active ingredient, 2–20% w/v emulsifiers and 0–20% w/v of other additives such as stabilisers, penetrants and corrosion inhibitors. Suspension concentrates are usually compounded so as to obtain a stable, non-sedimenting flowable product and usually contain 10–75% w/w active ingredient, 0.5–15% w/w of dispersing agents, 0.1–10% w/w of suspending agents such as protective colloids and thixotropic agents, 0–10% w/w of other additives such as defoamers, corrosion inhibitors, stabilisers, penetrants and stickers, and water or an organic liquid in which the active ingredient is substantially insoluble; certain organic solids or inorganic salts may be present dissolved in the formulation to assist in preventing sedimentation or as antifreeze agents for water.

Aqueous dispersions and emulsions, for example compositions obtained by diluting a wettable powder or a concentrate according to the invention with water, also lie within the scope of the invention. The said emulsions may be of the water-in-oil or of the oil-in-water type, and may have a thick 'mayonnaise'-like consistency.

The composition of the invention may also contain other ingredients, for example other compounds possessing herbicidal, insecticidal or fungicidal properties.

The invention is illustrated by the following Examples.

EXAMPLE 1

(R/S)-3-Isopropyl-[1,2,4]thiadiazole-5-Carboxylic Acid, [1-(2-Thienyl)ethyl]amide (a) 5-Isopropyl-[1,3,4]oxathiazolin-2-one Chlorocarbonyl sulphenyl chloride (41.9 g, 0.32 mol) is added dropwise to a stirred solution of isobutyramide (25.2 g, 0.29 mol) under dry nitrogen at room temperature. When the addition is complete, the mixture is refluxed for 8 hours, during which time hydrogen chloride gas is evolved. The solvent is removed in vacuo and the residue is distilled to give 5-isopropyl-[1,3,4]oxathiazolin-2-one (37 g, 88%) as a yellow oil, b.p. 58°–59° C./8 mmHg.

(b) Ethyl 3-Isopropyl-[1,2,4]thiadiazole-5-carboxylate

Ethyl cyanoformate (38.6 g, 0.39 mol) is added to a stirred solution of 5-isopropyl-[1,3,4]oxathiazolin-2-one (18.5 g, 0.13 mol) in p-xylene (180 ml). The mixture is refluxed for 6 hours and then the solvent is evaporated in vacuo to give crude ethyl 3-isopropyl-[1,2,4]thiadiazole-5-carboxylate (25.2 g, 97%) as a yellow oil, which is used without purification for the next step.

$^1$H NMR: 1.4–1.5 (3H, t and 6H, d); 3.4–3.5 (1H, m); 4.45–4.55 ppm, (2H, q).

(c) (R/S)-3-Isopropyl-[1,2,4]thiadiazole-5-carboxylic Acid, [1-(2-Thienyl)ethyl]amide (R/S)-1-Thiophen-2-yl-ethylamine (19.05 g, 0.150 mol) is added to a stirred solution of ethyl 3-isopropyl-[1,2,4]thiadiazole-5-carboxylate (25.0 g, 0.125 mol) in toluene (50 ml) and the mixture is heated to 80° C. for 2 hours. A further portion of (R/S)-1-[(2-thienyl)ethyl]amine (10.0 g, 0.08 mol) is added to the mixture, which is heated at 80° C. for a further 2 hours. Then a further portion of (R/S)-1-[(2-thienyl)ethyl]amine (10.0 g, 0.08 mol) is added to the mixture, and stirring is continued for a further 3 hours at 80° C. The solvent is evaporated in vacuo, and the residue is dissolved in methyl tert-butyl ether. The resulting solution is washed two times with 1N hydrochloric acid, dried with magnesium sulphate and the solvent is evaporated in vacuo. The oily residue is dissolved in petroleum ether (50 ml) and, upon agitation, the product crystallises out of the solution. The crystalline product is filtered off, washed with a small amount of petroleum ether and dried, to give (R/S)-3-isopropyl-[1,2,4]thiadiazole-5-carboxylic acid, [1-(2-thienyl)ethyl]amide (22.3 g, 63%) as beige crystals, m.p. 61°–63° C.

$^1$H NMR: 1.4 (6H, d); 1.7 (3H, d); 3.25–3.35 (1H, m); 5.5–5.6 (1H, q); 7.0 (1H, t); 7.1 (1H, d); 7.25 (1H, d); 7.4 ppm, (1H, d br).

EXAMPLE 2

(S)-3-(4-Methoxyphenyl)-[1,2,4]thiadiazole-5-carboxylic Acid (1-Phenylethyl)amide (a) 5-(4-Methoxyphenyl)-[1,3,4]oxathiazolin-2-one Chlorocarbonyl sulphenyl chloride (13.2 g, 0.10 mol) is added dropwise to a stirred solution of 4-methoxybenzamide (13.8 g, 0.091 mol) under dry nitrogen at room temperature. When the addition is complete, the mixture is refluxed for 8 hours, during which time hydrogen chloride gas is evolved. The solution is allowed to cool to room temperature and the solvent is removed in vacuo. The residue is triturated with methyl tert.-butyl ether and the crystalline solid is filtered off and dried, to give 5-(4-methoxyphenyl)-[1,3,4]oxathiazolin-2-one (12.2 g, 64%) as colourless crystals, m.p. 117°–118° C.

(b) Ethyl 3-(4-methoxyphenyl)-[1,2,4]thiadiazole-5-carboxylate

Ethyl cyanoformate (16.9 g, 0.171 mol) is added to a stirred solution of 5-(4-methoxyphenyl)-[1,3,4]oxathiazolin-2-one (11.9 g, 0.057 mol) in p-xylene (100 ml). The mixture is heated to 115°–132° C. for 10 hours, during which time carbon dioxide is liberated. The solvent is evaporated in vacuo and the residue is triturated with di-isopropyl ether. The crystalline solid is filtered off, washed with a small amount of diisopropyl ether and dried, to give ethyl 3-(4-methoxyphenyl)-[1,2,4]thiadiazole-5-carboxylate (11.6 g, 77%) as beige crystals, m.p. 61°–63° C.

(c) (S)-3-(4-Methoxyphenyl)-[1,2,4]thiadiazole-5-carboxylic Acid (1-(Phenylethyl)amide A mixture of (S)-1-phenylethyl)amine (1.21 g, 10 mmol) and ethyl 3-(4-methoxyphenyl)-[1,2,4]thiadiazole-5-carboxylate (1.32 g, 5 mmol) is stirred at 80° C. for 2 hours. A further portion of (S)-1-phenyl-ethylamine (0.5 g, 4 mmol) is added and the mixture is stirred for at 80° C. for a further 1.5 hours. The mixture is then cooled and dissolved in dichloromethane. The solution is washed with dilute sulphuric acid followed by water, and the organic phase is dried over magnesium sulphate. The solvent is evaporated in vacuo to give (S)-3-(4-methoxyphenyl)-[1,2,4]thiadiazole-5-carboxylic acid (1-phenylethyl)-amide (1.6 g, 94%) as colourless crystals, m.p. 143°–145° C.

$^1$H NMR: 1.6 (3H, d); 3.8 (3H, s); 5.2–5.3 (1H, q); 6.9 (2H, d); 7.2–7.4 (5H, m); 7.45 (1H, d br); 8.15 ppm, (2H, d).

EXAMPLE 3

(R/S)-5-(3-Trifluoromethylphenyl)-[1,2,4]thiadiazole-3-carboxylic Acid, [1-(2-Thienyl)ethyl]amide (a) Ethyl [1,3,4]Thioxazolin-2-one-5-carboxylate Chlorocarbonyl sulphenyl chloride (39.9 g, 0.34 mol) is added dropwise to a stirred solution of ethyl oxamate (50 g, 0.38 mol) in toluene (350 ml). The mixture is refluxed for 8 hours, then stirred overnight at room temperature. The solvent is evaporated in vacuo. The residue is taken up in toluene and the resulting solution is washed with sodium hydrogen carbonate solution and water. The organic phase is dried over anhydrous magnesium sulphate and the solvent is evaporated in vacuo. The oily residue is crystallised from petroleum ether to give ethyl [1,3,4]thioxazolin-2-one-5-carboxylate (38.6 g, 65%) as beige crystals, m.p. 45° C.

(b) 5-(3-Trifluoromethylphenyl)-[1,2,4]thiadiazole-3-carboxylate

A solution of ethyl [1,3,4]thioxazolin-2-one-5-carboxylate (3.0 g, 17 mmol) and 3-trifluoromethylbenzonitrile (11.64 g, 68 mmol) in 1,2-dichlorobenzene (12 ml) is refluxed for 4 days. The solvent is evaporated in vacuo and the residue is purified by flash column chromatography (silica gel, toluene followed by toluene/ethyl acetate 9:1 v/v) to give 5-(3-trifluoromethylphenyl)-[1,2,4]thiadiazole-3-carboxylate (1.45 g, 28%) as brown crystals, m.p. 94° C.

(c) (R/S)-5-(3-Trifluoromethylphenyl)-[1,2,4]thiadiazole-3-carboxylic Acid, [1-(2-Thienyl)ethyl]amide A solution of 5-(3-trifluoromethylphenyl)-[1,2,4]thiadiazole-3-carboxylate (0.9 g, 3.0 mmol) and (R/S)-1-[(2-thienyl)ethyl]amide (0.76 g, 6.0 mmol) in ethanol (25 ml) is stirred at room temperature for 4 days. The solvent is evaporated in vacuo and the residue is purified by flash column chromatography (silica gel, toluene/ethyl acetate 9:1 v/v). The oily residue is triturated with a small amount of petroleum ether and crystallises to give (R/S)-5-(3-trifluoromethylphenyl)-[1,2,4]thiadiazole-3-carboxylic acid, [1-(2-thienyl)ethyl]amide (0.80 g, 70%) as beige crystals, m.p. 149° C.

$^1$H NMR: 2.3–2.4 (3H, d); 5.7–5.8 (1H, q); 7.0 (1H, t); 7.2 (1H, d); 7.3 (1H, d); 7.7 (1H, t); 7.9 (1H, d); 8.2 (1H, d); 8.4 ppm, (1H, s).

Further examples of general formula I and II in which $R^1$ is H are prepared according to the methods of Examples 1–3 and are listed in Table 1. The structures of all products are confirmed by NMR spectroscopy.

TABLE 1

| Ex. No. | Cpd. Type | A | $R^2$ | Stereochem. | M. Pt. (°C.) |
|---|---|---|---|---|---|
| 4 | II | Phenyl | 2-Thienyl-CH(CH$_3$)— | (R/S) | 132–133 |
| 5 | II | Phenyl | Ph-CH(CH$_3$)— | (S) | 88–90 |
| 6 | II | tert-Butyl | 2-Thienyl-CH(CH$_3$)— | (R/S) | 106–108 |
| 7 | II | tert-Butyl | 2-Thienyl-CH$_2$— | — | 106–107 |
| 8 | II | tert-Butyl | Ph-CH(CH$_3$)— | (S) | oil |
| 9 | II | i-Propyl | 2-Thienyl-CH$_2$ | — | 51–52 |
| 10 | II | i-Propyl | Ph-CH(CH$_3$)— | (S) | oil |
| 11 | II | i-Butyl | 2-Thienyl-CH$_2$— | — | oil |
| 12 | II | i-Butyl | 2-Thienyl-CH(CH$_3$)— | (R/S) | oil |
| 13 | II | i-Butyl | Ph-CH(CH$_3$)— | (S) | oil |
| 14 | II | 4-F-Phenyl | 2-Thienyl-CH$_2$— | — | 122–125 |
| 15 | II | 4-F-Phenyl | 2-Thienyl-CH(CH$_3$)— | (R/S) | 101–103 |
| 16 | II | 4-F-Phenyl | Ph-CH(CH$_3$)— | (S) | 93–95 |
| 17 | II | 4-F-Phenyl | Ethyl | — | 114–116 |
| 18 | II | 4-F-Phenyl | CH$_2$=CHCH$_2$— | — | 76–77 |
| 19 | II | 4-F-Phenyl | i-Butyl | — | 115–117 |
| 20 | II | 4-F-Phenyl | PhCH$_2$— | — | 129–130 |
| 21 | II | 3-CF$_3$-Phenyl | 2-Thienyl-CH(CH$_3$)— | (R/S) | oil |
| 22 | I | Phenyl | 2-Thienyl-CH(CH$_3$)— | (R/S) | 150 |
| 23 | I | 4-Cl-Phenyl | 2-Thienyl-CH(CH$_3$)— | (R/S) | 101 |
| 24 | I | 4-Cl- | Ph-CH(CH$_3$)— | (S) | 86–88 |

TABLE 1-continued

Structure (I): S-N=C(A)-N=C-C(=O)NHR²  (thiadiazole isomer I)
Structure (II): N-S-C(A)=N-C-C(=O)NHR²  (thiadiazole isomer II)

| Ex. No. | Cpd. Type | A | R² | Stereo-chem. | M. Pt. (°C.) |
|---|---|---|---|---|---|
| 25 | II | n-Butyl | 2-Thienyl-CH(CH₃)— | (R/S) | oil |
| 26 | II | 4-Cl-Phenyl | 2-Thienyl-CH(CH₃)— | (R/S) | 106–120 |
| 27 | II | 4-Cl-Phenyl | Ph-CH(CH₃)— | (S) | 118–120 |
| 28 | II | Ph-CH=CH— | 2-Thienyl-CH₂— | — | 150–151 |
| 29 | II | Ph-CH=CH— | 2-Thienyl-CH(CH₃)— | (R/S) | 127–130 |
| 30 | II | Ph-CH=CH— | Ph-CH(CH₃)— | (S) | 97–99 |
| 31 | II | n-Butyl | 2-Thienyl-CH₂— | — | oil |
| 32 | II | n-Butyl | Ph-CH(CH₃)— | (S) | oil |
| 33 | II | MeO—CH₂CH₂— | 2-Thienyl-CH(CH₃)— | (R/S) | oil |
| 34 | II | MeO—CH₂CH₂— | Ph-CH(CH₃)— | (S) | oil |
| 35 | II | 4-MeO-Phenyl | 2-Thienyl-CH(CH₃)— | (R/S) | 102–104 |
| 36 | II | 4-MeO-Phenyl | 2-Thienyl-CH₂— | — | 115–117 |
| 37 | II | 4-MeO-Phenyl | (5-Methyl-2-thienyl)-CH(CH₃)— | (R/S) | 111–118 |
| 38 | II | 2-F-Phenyl | 2-Thienyl-CH(CH₃)— | (R/S) | 101–104 |
| 39 | I | 4-F-Phenyl | 2-Thienyl-CH(CH₃)— | (R/S) | 120 |
| 40 | I | 4-F-Phenyl | Ph-CH(CH₃)— | (S) | 112 |
| 41 | I | 4-Me-Phenyl | 2-Thienyl-CH(CH₃)— | (R/S) | 130–132 |
| 42 | I | 3-CF₃-Phenyl | Ph-CH(CH₃)— | (S) | 118 |
| 43 | II | 3-F-Phenyl | 2-Thienyl-CH(CH₃)— | (R/S) | 132–135 |
| 44 | II | 3-F-Phenyl | 2-Thienyl-CH₂— | — | 141–143 |
| 45 | II | 3-F-Phenyl | Ph-CH(CH₃)— | (S) | 74–75 |
| 46 | II | 6-Cl-2-Pyridyl | Ph-CH(CH₃)— | (S) | oil |
| 47 | II | 6-Cl-2-Pyridyl | 2-Thienyl-CH(CH₃)— | (R/S) | 96–100 |
| 48 | I | Phenyl | Ph-CH(CH₃)— | (S) | 102 |
| 49 | I | Phenyl | 2-Thienyl-CH₂— | — | 134–136 |
| 50 | II | 2-F-Phenyl | 2-Thienyl-CH₂— | — | 162–164 |
| 51 | I | 4-MeO-Phenyl | 2-Thienyl-CH(CH₃)— | (R/S) | 95–97 |
| 52 | II | i-Propyl | 2-Thienyl-CH(CH₃)— | (R/S) | 84–85 |
| 53 | II | 2-F-Phenyl | 1-(1,2,3,4-Tetrahydronaphthalen)-yl | (R/S) | 149–151 |
| 54 | II | 4-MeO-Phenyl | 1-(1,2,3,4-Tetrahydronaphthalen)-yl | (R/S) | 161–162 |
| 55 | II | 4-MeO-Phenyl | 5-(1,2,3,4-Tetrahydronaphthalen)-yl | (R/S) | 133–135 |
| 56 | I | 2-F-Phenyl | Ph-CH(CH₃)— | (S) | 101 |
| 57 | I | 2-F-Phenyl | 2-Thienyl-CH(CH₃)— | (R/S) | 133–135 |
| 58 | II | 2,6-di-F-Phenyl | 2-Thienyl-CH(CH₃)— | (R/S) | 94–96 |
| 59 | II | 2,6-di-F-Phenyl | Ph-CH(CH₃)— | (S) | 89–90 |
| 60 | II | 2,6-di-F-Phenyl | 2-Thienyl-CH₂— | — | 90–91 |
| 61 | II | 4-MeO-Phenyl | 3-Thienyl-CH(CH₃)— | (R/S) | 141–143 |

TABLE 1-continued

Structures (I) and (II) of thiadiazole/thiazole carboxamide compounds with substituent A and NHR².

| Ex. No. | Cpd. Type | A | R² | Stereo-chem. | M. Pt. (°C.) |
|---|---|---|---|---|---|
| 62 | I | 3-CF₃-Phenyl | 2,4-di-F-Phenyl | — | 204 |
| 63 | I | 3-CF₃-Phenyl | 4-F-Phenyl | — | 185 |
| 64 | I | 3-CF₃-Phenyl | Phenyl | — | 174 |
| 65 | I | 3-CF₃-Phenyl | 3-F-Phenyl | — | 190 |

EXAMPLE 66

Herbicidal Activity

To evaluate their herbicidal activity, compounds according to the invention are tested using a representative range of plants:

| | |
|---|---|
| ZEAMX | *Zea mays* |
| ORYSA | *Oryza sativa* |
| GLXMA | *Glycine max* |
| BEAVA | *Beta vulgaris* |
| LIUUT | *Linum usitatissimum* |
| AVEFA | *Avena fatua* |
| ECHCG | *Echinochloa crus-galli* |
| SINAL | *Sinapsis alba* |

The tests fall into two categories, preemergence and postemergence. The preemergence tests involve spraying a liquid formulation of the compound onto the soil in which the seeds of the plant species mentioned above have recently been sown. The postemergence tests involve spraying a liquid formulation of the compound onto seedling plants of the above species.

The soil used in the tests is a prepared horticultural loam.

The formulations used in the tests are prepared from solutions of the test compounds in acetone containing 0.4% by weight of an alkylphenol/ethylene oxide condensate available under the trademark TRITON X-155. These acetone solutions are diluted with water and the resulting formulations applied at dosage levels corresponding to 1000 g of active material per hectare in a volume equivalent to 900 liters per hectare.

In the preemergence tests, untreated sown soil, and in the postemergence tests, untreated soil bearing seedling plants, are used as controls.

The herbicidal effects of the test compounds are assessed visually twenty days after spraying the foliage and the soil and are recorded on a 0–9 scale. A rating of 0 indicates growth as untreated control, a rating of 9 indicates death. An increase of 1 unit on the linear scale approximates to an 11% increase in the level of effect.

The results of the tests are set out in Table 2.

TABLE 2

| Ex. No. | Dose g/ha | Appl. Time | ZEAMX | ORYSA | GLXMA | BEAVA | LIUUT | AVEFA | ECHCG | SINAL |
|---|---|---|---|---|---|---|---|---|---|---|
| 1 | 1000 | pre | 0 | 0 | 0 | 7 | 2 | 2 | 5 | 7 |
|   |      | post | 0 | 0 | 6 | 9 | 9 | 5 | 9 | 9 |
| 4 | 1000 | pre | 0 | 0 | 0 | 0 | 0 | 0 | 0 | 0 |
|   |      | post | 0 | 0 | 5 | 8 | 7 | 5 | 8 | 8 |
| 5 | 1000 | pre | 0 | 0 | 0 | 4 | 0 | 0 | 0 | 0 |
|   |      | post | 2 | 0 | 4 | 5 | 7 | 6 | 8 | 9 |
| 6 | 1000 | pre | 0 | 0 | 0 | 9 | 3 | 0 | 0 | 7 |
|   |      | post | 0 | 2 | 7 | 9 | 9 | 7 | 9 | 9 |
| 7 | 1000 | pre | 0 | 0 | 0 | 0 | 0 | 0 | 0 | 0 |
|   |      | post | 0 | 0 | 3 | 8 | 4 | 0 | 0 | 8 |
| 8 | 1000 | pre | 0 | 0 | 0 | 8 | 0 | 0 | 0 | 8 |
|   |      | post | 0 | 0 | 6 | 9 | 9 | 6 | 8 | 9 |
| 9 | 1000 | pre | 0 | 0 | 0 | 0 | 0 | 0 | 2 | 4 |
|   |      | post | 2 | 0 | 2 | 7 | 2 | 0 | 5 | 7 |
| 10 | 1000 | pre | 0 | 0 | 0 | 7 | 4 | 0 | 5 | 7 |
|    |      | post | 2 | 0 | 5 | 8 | 8 | 5 | 8 | 8 |
| 11 | 1000 | pre | 0 | 0 | 0 | 0 | 0 | 0 | 0 | 0 |
|    |      | post | 0 | 0 | 2 | 4 | 2 | 0 | 2 | 7 |
| 12 | 1000 | pre | 0 | 0 | 0 | 5 | 2 | 0 | 5 | 5 |
|    |      | post | 0 | 0 | 5 | 8 | 8 | 2 | 9 | 9 |
| 13 | 1000 | pre | 0 | 0 | 0 | 5 | 0 | 0 | 2 | 4 |
|    |      | post | 2 | 0 | 5 | 9 | 7 | 5 | 8 | 8 |

TABLE 2-continued

| Ex. No. | Dose g/ha | Appl. Time | ZEAMX | ORYSA | GLXMA | BEAVA | LIUUT | AVEFA | ECHCG | SINAL |
|---|---|---|---|---|---|---|---|---|---|---|
| 14 | 1000 | pre | 0 | 0 | 0 | 0 | 0 | 0 | 0 | 0 |
|  |  | post | 0 | 0 | 2 | 8 | 5 | 0 | 2 | 8 |
| 15 | 1000 | pre | 0 | 0 | 0 | 0 | 0 | 0 | 0 | 0 |
|  |  | post | 3 | 0 | 7 | 9 | 7 | 4 | 7 | 9 |
| 16 | 1000 | pre | 0 | 0 | 0 | 0 | 0 | 0 | 0 | 0 |
|  |  | post | 0 | 2 | 6 | 9 | 7 | 7 | 8 | 9 |
| 17 | 1000 | pre | 0 | 0 | 0 | 0 | 0 | 0 | 0 | 0 |
|  |  | post | 2 | 0 | 5 | 7 | 2 | 4 | 2 | 8 |
| 18 | 1000 | pre | 0 | 0 | 0 | 0 | 0 | 0 | 0 | 0 |
|  |  | post | 0 | 0 | 6 | 8 | 5 | 2 | 0 | 9 |
| 19 | 1000 | pre | 0 | 0 | 0 | 0 | 0 | 0 | 0 | 0 |
|  |  | post | 0 | 0 | 6 | 8 | 2 | 0 | 0 | 8 |
| 20 | 1000 | pre | 0 | 0 | 0 | 0 | 0 | 0 | 0 | 0 |
|  |  | post | 0 | 0 | 6 | 9 | 6 | 0 | 2 | 9 |
| 21 | 1000 | pre | 0 | 0 | 0 | 0 | 0 | 0 | 0 | 0 |
|  |  | post | 0 | 0 | 7 | 8 | 7 | 7 | 8 | 9 |
| 22 | 1000 | pre | 1 | 0 | 0 | 2 | 0 | 0 | 2 | 3 |
|  |  | post | 2 | 2 | 6 | 9 | 6 | 4 | 5 | 7 |
| 23 | 1000 | pre | 0 | 0 | 0 | 0 | 0 | 0 | 0 | 0 |
|  |  | post | 0 | 0 | 7 | 9 | 7 | 4 | 8 | 9 |
| 24 | 1000 | pre | 0 | 0 | 0 | 0 | 0 | 0 | 0 | 0 |
|  |  | post | 0 | 0 | 5 | 8 | 5 | 0 | 2 | 8 |

EXAMPLE 67

Herbicidal Activity

Herbicidal evaluation of compounds of the invention is conducted on the following plant species:

| Column Heading | Scientific Name |
|---|---|
| TRZAW | *Triticum aestivum* |
| HORVW | *Hordeum vulgare* |
| ZEAMX | *Zea mays* |
| HELAN | *Helianthus annuus* |
| ALOMY | *Alopecurus myosuroides* |
| SETVI | *Setaria viridis* |
| GALAP | *Galium aparine* |
| VERPE | *Veronica persica* |
| IPOHE | *Ipomoea hederacea* |
| AMARE | *Amaranthus retroflexus* |
| ABUTH | *Abutilon theophrasti* |
| CHEAL | *Chenopodium album* |

The postemergence herbicidal activity of test compounds is demonstrated using seedling plants grown in plastic flats for about 3–6 weeks. The soil is a prepared horticultural substrate containing 30% peat, 20% volcanic clay, 30% bark residues and 20% polyamide/styromull in a 1:3 mixture with loamy sand. Test solutions are prepared by dissolving the test compound in acetone containing 0.5% of an alkylphenol/ethylene oxide condensate under the trademark, TRITON® X-155, and diluting with water as needed. The test solutions are applied as a spray to the 3–6 week old seedling plants at dose rates corresponding to 800 g/ha in a volume equivalent to 400 L/ha. A pneumatic spraying device employing a Teejet nozzle SS 8002E operating at 3 bar is used for a predetermined time. After spraying, the treated plants are placed on greenhouse benches and cared for in a manner commensurate with conventional greenhouse practice. After 10–21 days, the treated plants are evaluated and rated according to the rating system provided below.

| Herbicide Rating Scale | |
|---|---|
| Rating | Definition |
| 9 | 100% effect |
| 8 | 91–99% |
| 7 | 80–90% |
| 6 | 65–79% |
| 5 | 45–64% |
| 4 | 30–44% |
| 3 | 16–29% |
| 2 | 6–15% |
| 1 | 1–5% |
| 0 | No herbicidal effect |

The preemergence herbicidal activity of the test compounds is demonstrated by the following method in which the seeds of a variety of plant species are separately mixed with potting soil and sown on the surface of about 0.5–3.0 am of soil in a one pint cup. The soil surface is then sprayed with test solutions as described in the postemergence evaluation hereinabove. After spraying, the treated cups are placed on greenhouse benches and cared for in the manner commensurate with conventional greenhouse practice. About 1–3 weeks after treatment the cups are evaluated and rated according to the rating system provided hereinabove. The postemergence and preemergence test results are shown in Table 3.

TABLE 3

| Ex. No. | Dose g/h | Appl Time | TRZ AW | HOR VW | ZEA MX | HEL AN | ALO MY | SET VI | GAL AP | VER PE | IPO HE | AMA RE | ABU TH | CHE AL |
|---|---|---|---|---|---|---|---|---|---|---|---|---|---|---|
| 2 | 800 | pre | 0 | 0 | 0 | 0 | 0 | 0 | 0 | 0 | 5 | 0 | 0 | 0 |
|  |  | pos | 2 | 2 | 1 | 1 | 2 | 5 | 0 | 0 | 2 | 0 | 1 | 3 |
| 3 | 800 | pre | 0 | 0 | 0 | 0 | 0 | 0 | 0 | 0 | 0 | 0 | 0 | 3 |

TABLE 3-continued

| Ex. No. | Dose g/h | Appl Time | TRZ AW | HOR VW | ZEA MX | HEL AN | ALO MY | SET VI | GAL AP | VER PE | IPO HE | AMA RE | ABU TH | CHE AL |
|---|---|---|---|---|---|---|---|---|---|---|---|---|---|---|
|  |  | pos | 2 | 2 | 1 | 4 | 3 | 8 | 2 | 0 | 3 | 2 | 1 | 4 |
| 25 | 800 | pre | 0 | 0 | 0 | 0 | 0 | 0 | 0 | 4 | 0 | 0 | 0 | 6 |
|  |  | pos | 2 | 3 | 0 | 7 | 4 | 8 | 6 | 3 | 5 | 3 | 6 | 6 |
| 26 | 800 | pre | 0 | 0 | 0 | 0 | 0 | 0 | 0 | 2 | 0 | 0 | 0 | 3 |
|  |  | pos | 2 | 3 | 4 | 7 | 2 | 5 | 5 | 4 | 6 | 6 | 5 | 5 |
| 27 | 800 | pre | 0 | 0 | 0 | 3 | 0 | 0 | 0 | 7 | 1 | 0 | 0 | 2 |
|  |  | pos | 2 | 2 | 5 | 8 | 4 | 8 | 5 | 7 | 7 | 5 | 6 | 4 |
| 28 | 800 | pre | 0 | 0 | 0 | 0 | 0 | 0 | 0 | 0 | 0 | 0 | 0 | 0 |
|  |  | pos | 0 | 0 | 0 | 0 | 1 | 3 | 0 | 2 | 0 | 0 | 1 | 2 |
| 29 | 800 | pre | 0 | 0 | 0 | 0 | 0 | 0 | 0 | 0 | 0 | 0 | 0 | 4 |
|  |  | pos | 0 | 0 | 0 | 4 | 2 | 4 | 1 | 0 | 4 | 1 | 1 | 3 |
| 30 | 800 | pre | 0 | 0 | 0 | 0 | 0 | 0 | 0 | 0 | 0 | 0 | 2 | 0 |
|  |  | pos | 2 | 0 | 0 | 2 | 1 | 3 | 4 | 0 | 4 | 2 | 3 | 4 |
| 31 | 800 | pre | 0 | 0 | 0 | 0 | 0 | 0 | 0 | 0 | 0 | 0 | 0 | 0 |
|  |  | pos | 2 | 0 | 1 | 2 | 2 | 4 | 2 | 0 | 3 | 0 | 1 | 4 |
| 32 | 800 | pre | 0 | 0 | 0 | 0 | 0 | 0 | 0 | 5 | 0 | 0 | 0 | 5 |
|  |  | pos | 3 | 2 | 0 | 5 | 2 | 7 | 6 | 0 | 5 | 3 | 5 | 5 |
| 33 | 800 | pre | 0 | 0 | 0 | 0 | 0 | 0 | 0 | 5 | 0 | 0 | 0 | 2 |
|  |  | pos | 2 | 3 | 0 | 4 | 3 | 6 | 3 | 0 | 4 | 0 | 2 | 2 |
| 34 | 800 | pre | 0 | 0 | 0 | 0 | 0 | 0 | 0 | 3 | 0 | 0 | 0 | 0 |
|  |  | pos | 3 | 0 | 0 | 2 | 3 | 3 | 1 | 2 | 4 | 0 | 1 | 2 |
| 35 | 800 | pre | 0 | 0 | 0 | 3 | 0 | 0 | 4 | 4 | 0 | 0 | 0 | 5 |
|  |  | pos | 3 | 3 | 3 | 5 | 3 | 8 | 4 | 2 | 4 | 3 | 4 | 5 |
| 36 | 800 | pos | 0 | 0 | 3 | 0 | 0 | 0 | 0 | 0 | 2 | 0 | 0 | 0 |
|  |  | pos | 3 | 0 | 4 | 3 | 7 | 2 | 2 | 3 | 2 | 1 | 3 |  |
| 37 | 800 | pre | 0 | 0 | 0 | 0 | 0 | 0 | 0 | 0 | 0 | 0 | 0 | 6 |
|  |  | pos | 3 | 2 | 0 | 0 | 2 | 4 | 0 | 0 | 1 | 0 | 0 | 3 |
| 38 | 800 | pre | 0 | 0 | 0 | 0 | 0 | 0 | 0 | 2 | 0 | 4 | 0 | 5 |
|  |  | pos | 3 | 3 | 3 | 7 | 4 | 8 | 5 | 1 | 5 | 3 | 8 | 6 |
| 39 | 800 | pre | 0 | 0 | 0 | 0 | 0 | 0 | 0 | 0 | 0 | 4 | 0 | 0 |
|  |  | pos | 3 | 3 | 6 | 6 | 3 | 8 | 5 | 2 | 4 | 3 | 4 | 4 |
| 40 | 800 | pre | 0 | 0 | 0 | 4 | 0 | 4 | 0 | 5 | 0 | 0 | 8 | 4 |
|  |  | pos | 4 | 6 | 5 | 9 | 5 | 9 | 8 | 8 | 8 | 8 | 8 | 8 |
| 41 | 800 | pre | 0 | 0 | 4 | 0 | 0 | 0 | 0 | 3 | 0 | 0 | 0 | 3 |
|  |  | pos | 2 | 2 | 2 | 5 | 2 | 8 | 3 | 0 | 3 | 3 | 1 | 5 |
| 42 | 800 | pos | 0 | 0 | 0 | 0 | 0 | 0 | 2 | 2 | 0 | 0 | 0 | 5 |
|  |  | pos | 2 | 2 | 0 | 3 | 1 | 5 | 0 | 0 | 2 | 0 | 0 | 3 |
| 43 | 800 | pre | 0 | 0 | 0 | 0 | 0 | 0 | 2 | 2 | 2 | 0 | 0 | 4 |
|  |  | pos | 2 | 2 | 0 | 3 | 1 | 3 | 2 | 2 | 2 | 0 | 1 | 4 |
| 44 | 800 | pre | 0 | 0 | 0 | 0 | 4 | 3 | 0 | 0 | 3 | 0 | 0 | 0 |
|  |  | pos | 3 | 3 | 2 | 0 | 0 | 3 | 3 | 0 | 3 | 0 | 0 | 0 |
| 45 | 800 | pre | 0 | 0 | 0 | 0 | 3 | 0 | 0 | 8 | 0 | 0 | 0 | 0 |
|  |  | pos | 3 | 4 | 4 | 8 | 4 | 6 | 6 | 7 | 8 | 3 | 8 | 8 |
| 46 | 800 | pre | 1 | 0 | 0 | 0 | 0 | 0 | 0 | 5 | 0 | 5 | 0 | 4 |
|  |  | pos | 5 | 6 | 5 | 8 | 6 | 8 | 5 | 8 | 8 | 3 | 8 | 6 |
| 47 | 800 | pre | 0 | 0 | 0 | 0 | 0 | 3 | 1 | 0 | 1 | 0 | 2 | 0 |
|  |  | pos | 1 | 3 | 4 | 5 | 4 | 6 | 4 | 3 | 4 | 1 | 4 | 4 |
| 48 | 800 | pre | 2 | 0 | 0 | 0 | 0 | 0 | 0 | 5 | 0 | 5 | 0 | 0 |
|  |  | pos | 5 | 7 | 5 | 9 | 6 | 8 | 7 | 8 | 7 | 7 | 8 | 7 |
| 49 | 800 | pre | 0 | 0 | 0 | 1 | 0 | 0 | 0 | 0 | 0 | 0 | 0 | 0 |
|  |  | pos | 3 | 4 | 4 | 8 | 5 | 8 | 6 | 3 | 3 | 3 | 4 | 4 |
| 50 | 800 | pre | 0 | 1 | 0 | 0 | 3 | 0 | 0 | 0 | 0 | 0 | 0 | 0 |
|  |  | pos | 1 | 2 | 0 | 3 | 0 | 5 | 2 | 0 | 0 | 0 | 0 | 3 |
| 51 | 800 | pre | 2 | 2 | 0 | 1 | 3 | 0 | 0 | 0 | 0 | 5 | 3 | 0 |
|  |  | pos | 3 | 5 | 5 | 8 | 5 | 8 | 6 | 8 | 8 | 4 | 6 | 4 |
| 52 | 800 | pre | 0 | 0 | 0 | 0 | 0 | 2 | 0 | 9 | 0 | 7 | 0 | 0 |
|  |  | pos | 4 | 5 | 5 | 9 | 5 | 8 | 6 | 8 | 8 | 6 | 8 | 6 |
| 53 | 800 | pos | 1 | 0 | 0 | 0 | 0 | 0 | 0 | 6 | 0 | 3 | 0 | 0 |
|  |  | pos | 2 | 2 | 0 | 0 | 1 | 5 | 2 | 0 | 2 | 0 | 0 | 0 |
| 54 | 800 | pre | 0 | 0 | 0 | 0 | 0 | 0 | 0 | 0 | 0 | 0 | 0 | 0 |
|  |  | pos | 1 | 3 | 4 | 4 | 2 | 3 | 3 | 0 | 2 | 0 | 2 | 2 |
| 55 | 800 | pre | 0 | 0 | 0 | 0 | 0 | 0 | 0 | 2 | 3 | 0 | 1 | 0 |
|  |  | pos | 1 | 2 | 3 | 2 | 0 | 4 | 3 | 0 | 0 | 0 | 0 | 0 |
| 56 | 800 | pre | 0 | 0 | 0 | 0 | 0 | 2 | 0 | 4 | 3 | 5 | 2 | 2 |
|  |  | pos | 5 | 5 | 4 | 8 | 5 | 8 | 6 | 7 | 8 | 7 | 9 | 4 |
| 57 | 800 | pre | 2 | 0 | 0 | 0 | 3 | 2 | 0 | 0 | 0 | 4 | 0 | 1 |
|  |  | pos | 3 | 4 | 5 | 8 | 4 | 9 | 7 | 6 | 7 | 7 | 9 | 4 |
| 58 | 800 | pre | 0 | 0 | 0 | 0 | * | 0 | 0 | 0 | * | 0 | * | 0 |
|  |  | pos | 2 | 3 | 0 | 9 | * | 2 | 6 | 4 | * | 7 | * | 6 |
| 59 | 800 | pre | 0 | 0 | 0 | 0 | * | 3 | 3 | 6 | * | 3 | * | 0 |
|  |  | pos | 3 | 3 | 0 | 6 | * | 3 | 6 | 8 | * | 8 | * | 7 |
| 60 | 800 | pre | 0 | 0 | 0 | 0 | * | 0 | 0 | 0 | * | 0 | * | 0 |
|  |  | pos | 0 | 0 | 3 | 3 | * | 0 | 0 | 0 | * | 5 | * | 0 |
| 61 | 800 | pre | 0 | 0 | 0 | 0 | 0 | 0 | 0 | 0 | 0 | 0 | 0 | * |
|  |  | pos | 0 | 0 | 0 | 2 | 1 | 0 | 0 | 0 | 0 | 0 | 0 | * |
| 62 | 800 | pre | 0 | 0 | 0 | 0 | 3 | 0 | 0 | 0 | 3 | 0 | 1 | 0 |

TABLE 3-continued

| Ex. No. | Dose g/h | Appl Time | TRZ AW | HOR VW | ZEA MX | HEL AN | ALO MY | SET VI | GAL AP | VER PE | IPO HE | AMA RE | ABU TH | CHE AL |
|---|---|---|---|---|---|---|---|---|---|---|---|---|---|---|
|  |  | pos | 1 | 0 | 1 | 0 | 0 | 5 | 0 | 0 | 1 | 0 | 0 | 1 |
| 63 | 800 | pre | 2 | 0 | 0 | 0 | 4 | 2 | 0 | 0 | 3 | 0 | 0 | 0 |
|  |  | pos | 0 | 1 | 0 | 0 | 0 | 3 | 0 | 0 | 0 | 0 | 1 | 0 |
| 64 | 800 | pre | 2 | 0 | 0 | 0 | 0 | 2 | 0 | 0 | 3 | 0 | 0 | 0 |
|  |  | pos | 2 | 1 | 1 | 0 | 2 | 4 | 0 | 0 | 0 | 0 | 1 | 0 |
| 65 | 800 | pre | 2 | 0 | 0 | 0 | 4 | 0 | 0 | 0 | 3 | 0 | 3 | 1 |
|  |  | pos | 3 | 1 | 0 | 0 | 1 | 0 | 0 | 0 | 1 | 0 | 0 | 0 |

I claim:

1. A compound of the general formula

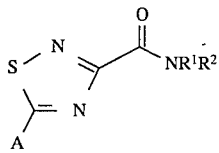

(I)

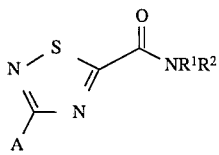

(II)

wherein

A represents $C_{2-6}$ alkyl optionally substituted with one or more halogen, nitro, cyano, hydroxyl, $C_{1-4}$alkoxy, $C_{1-4}$haloalkoxy, ($C_{1-4}$ alkoxy) carbonyl, phenyl, amino, alkylsulphinyl, alkylsulphenyl, alkylsulphonyl, phenylsulphinyl, phenylsulphenyl, phenylsulphonyl, or mono- or di-($C_{1-4}$ alkyl)amino groups;

$C_{2-6}$ alkenyl optionally substituted with one or more halogen, nitro, cyano, hydroxyl, $C_{1-4}$alkoxy, $C_{1-4}$haloalkoxy, ($C_{1-4}$ alkoxy)carbonyl, phenyl, amino, alkylsulphinyl, alkylsulphenyl, alkylsulphonyl, phenylsulphinyl, phenylsulphenyl, phenylsulphonyl, or mono- or di-($C_{1-4}$ alkyl)amino groups;

phenyl optionally substituted with one or more moieties independently selected from the group consisting of halogen atoms, $C_{1-4}$ alkyl groups, $C_{1-4}$ alkoxy groups, and $C_{1-4}$ haloalkyl groups;

pyridine optionally substituted with one or more halogen;

$R_1$ represents a hydrogen atom or an acyl group;

$R_2$ represents —$CH(R^3)R^4$;

$R_3$ represents a hydrogen atom or a $C_{1-2}$ alkyl group optionally substituted with one or more halogen, nitro, cyano, hydroxyl, $C_{1-4}$alkoxy, $C_{1-4}$haloalkoxy, ($C_{1-4}$ alkoxy)carbonyl, phenyl, amino, alkylsulphinyl, alkylsulphenyl, alkylsulphonyl, phenylsulphinyl, phenylsulphonyl, or mono- or di-($C_{1-4}$ alkyl)amino groups;

$R_4$ represents an optionally substituted phenyl, optionally substituted pyridyl, optionally substituted furyl, optionally substituted thienyl, or optionally substituted benzothienyl group wherein said optional substitutents are selected from the group consisting of halogen, nitro, cyano, amino, hydroxyl, $C_{1-4}$ alkyl, $C_{1-4}$ haloalkyl, $C_{1-4}$ alkoxy and $C_{1-4}$ haloalkoxy groups.

2. A compound as claimed in claim 1, wherein

A represents a tert-butyl, isobutyl, isopropyl, 2-methoxyethyl, styryl, phenyl optionally subsituted with one or two moieties selected from fluorine, chlorine, trifluoromethyl and methoxy groups, or pyridyl optionally subsituted by chlorine.

3. A herbicidal composition comprising a compound of formula I or II, as defined in claim 1 together with a carrier.

4. A composition as claimed in claim 3, comprising at least two carriers, at least one of which is a surface-active agent.

5. A method of combating undesired plant growth at a locus, comprising application to the locus of a compound of general formula I or II, as claimed in claim 1 or of a composition as claimed in claim 3.

6. The compound according to claim 1 wherein $R^1$ is hydrogen.

* * * * *